US006495536B1

(12) United States Patent
Masui et al.

(10) Patent No.: US 6,495,536 B1
(45) Date of Patent: Dec. 17, 2002

(54) FAT OR OIL COMPOSITION

(75) Inventors: Kenji Masui; Yoshihisa Katsuragi; Tomoko Toi; Takuji Yasukawa, all of Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/427,081

(22) Filed: Oct. 26, 1999

(30) Foreign Application Priority Data

Aug. 24, 1999 (JP) ............................................ 11-237556

(51) Int. Cl.$^7$ ........................ A61K 31/56; A61K 31/20
(52) U.S. Cl. ...................................... 514/182; 514/560
(58) Field of Search .................................. 514/560, 182

(56) References Cited

U.S. PATENT DOCUMENTS

| | | | |
|---|---|---|---|
| 4,656,045 A | 4/1987 | Bodor et al. ................ | 426/601 |
| 4,976,984 A | 12/1990 | Yasukawa et al. .......... | 426/602 |
| 5,077,077 A | 12/1991 | Suzuki et al. ............... | 426/602 |
| 5,879,735 A | 3/1999 | Cain et al. .................. | 426/603 |
| 6,004,611 A | 12/1999 | Gotoh et al. ................ | 426/612 |
| 6,025,348 A | 2/2000 | Goto et al. .................. | 514/182 |
| 6,139,897 A | * 10/2000 | Goto et al. .................. | 426/601 |
| 6,337,414 B1 | 1/2002 | Sugiura et al. .............. | 554/174 |

FOREIGN PATENT DOCUMENTS

| | | |
|---|---|---|
| EP | 0 171 112 A1 | 2/1986 |
| EP | 0 836 805 A1 | 4/1998 |
| EP | 0 990 391 A1 | 4/2000 |
| JP | 7-61954 | 7/1995 |
| WO | WO 96/32022 | 10/1996 |
| WO | WO 98/01461 | 1/1998 |
| WO | WO 01/01787 | 1/2001 |
| WO | WO 01/15542 | 3/2001 |

OTHER PUBLICATIONS

New England Journal of Medicine, vol. 340, No. 25, 11 pages, "Trans Fatty Acids and Coronary Heart Disease," Jun. 24, 1999.

Effects of Different Forms of Dietary Hydrogenated Fats on Serum Lipoprotein Cholesterol Levels, The New England Journal of Medicine, vol. 340, Jun. 24, 1999, No. 25, Alice H. Lichtenstein, D.Sc., Lynne M. Ausman, D.Sc., Susan M. Jalbert, M.L.T., and Ernst J. Schaefer, M.D., pp. 1933–1940.

Trans Fatty Acids and Coronary Heart Disease, Sounding Board, Massachusetts Medical Society http://www/mej–m.org/content/figs/1999/0025/1994.asp?section=F1[Jul. 1, 1999 8:52:30].

Trans Fatty Acids and Coronary Heart Disease, Sounding Board, Massachusetts Medical Society http://www/mej–m.org/content/refs/1999/0340/1994.asp(4/4)[Jul. 1, 1999 8:51:38].

FDA Proposes New Rules for Trans Fatty Acids in Nutrition Labeling, Nutrient Content Claims, and Health Claims, HHS NEWS, U.S. Department of Health and Human Services P99–27, Nov. 12, 1999, http://vm.cfsan.fda.gov/~lrd/.

Questions and Answers on Trans Fat Proposed Rule, Press Release and Fact Sheet on Trans Fat Proposed Rule, U.S. Food and Drug Administration Center for Food Safety and Applied Nutrition, Office of Labeling, Nov. 1999, NEWS, U.S. Department of Health and Human Services P99–27, Nov. 12, 1999, http://vm.cfsan.fda.gov/~dms/.

Trans Fatty Acids, Plasma Lipid Levels, and Risk of Developing Cardiovascular Disease, A Statement for Healthcare Professions From the American Heart Association, Alice H. Lichtenstein, DSc, for the Nutrition Committee, American Heart Association, Circulation 1997;95:2588–2590, 1997 American Heart Association, Inc.

Trans Fatty Acids, 1999*American* Heart Association.

J.A. Weststrate, et al., "Plant sterol–enriched margarines and reduction of plasma total–and LDL –cholesterol concentrations in normocholesterolaemic and mildly hypercholesterolaemic subjects", JOURNAL OF CLINICAL NUTRITION, vol. 52, No. 5, pp. 334–343, 1998. XP–000884738.

T. Kooistra, et al., "Role of Protein Kinase C And Cyclic AMP in the Regulation of Tissue–type Plasminogen Activator Plasminogen Activator Inhibitor–1 and Platelet–derived Growth Factor Messenger RNA Levels in Human Endothelial Cells Possible Involvement of Proto–oncogenes C–JUN and C–FOS", Arteriosclerosis and Thrombosis, vol. 11, No. 4, pp. 1042–1052, 1991. Abstract Only. XP–002153095.

W. H. Ling, et al., "Enhanced efficacy of sitostanol–containing versus sitostanol–free phytosterol mixtures in altering lipoprotein cholesterol levels and synthesis in rats", Atherosclerosis, vol. 118, No. 2, pp. 319–331, 1995. XP–002055615.

\* cited by examiner

*Primary Examiner*—Theodore J. Criares
*Assistant Examiner*—Jennifer Kim
(74) *Attorney, Agent, or Firm*—Oblon, Spivak, McClelland, Maier & Neustadt, P.C.

(57) ABSTRACT

Described is a fat or oil composition which comprises at least 35 wt. % of a diacylglycerol, the constituent fatty acids of said diacylglycerol satisfying the following equation: (an amount of a cis-form unsaturated fatty acid)/(an amount of a saturated fatty acid+an amount of a trans-form unsaturated fatty acid)$\geq 6$. Usual intake of the above-described composition as an edible oil makes it possible to reduce arteriosclerotic factors in blood, leading to the prevention of arteriosclerosis, furthermore, various degenerative diseases.

16 Claims, No Drawings

FAT OR OIL COMPOSITION

BACKGROUND OF THE INVENTION

1. Field of the Invention

The present invention relates to a fat or oil composition capable of reducing arteriosclerotic factors in blood when taken, similarly to a usual fat or oil, in the daily life.

2. Description of the Related Art

Arteriosclerosis is a risk factor of various circulatory diseases such as hypertension and thrombosis. Arteriosclerosis is caused by hypercholesterolemia, formation of thrombus or the like. The state of a high total cholesterol level is generally called hypercholesterolemia. The cholesterol in blood is classified into HDL, LDL, VLDL and the like by specific gravity. Among them, LDL is a principal risk factor of arteriosclerosis, while HDL is said to be useful for the prevention of arteriosclerosis. It is therefore important to increase the HDL cholesterol level in blood for the prevention of arteriosclerosis.

On the other hand, local formation of thrombi in blood is also considered as one of the factors of arteriosclerosis. When the activity of plasminogen activator inhibitor type 1 (PAI-1) which serves to control the production of plasmin, that is, fibrinolysin in blood is exasperated, the production of plasmin is suppressed and formation of thrombi tends to occur. It is therefore essential to lower the activity of PAI-1 for the prevention of arteriosclerosis.

With regards to arteriosclerosis, prevention by the daily dietary control is more important than treatment. There is accordingly a demand for a substance which can be taken easily in the daily life and at the same time, can reduce the above-described arteriosclerotic factor.

SUMMARY OF THE INVENTION

Paying attention to a diacylglycerol which is known to suppress a postprandial increase in the blood level of a neutral fat, the present inventors have investigated constituent fatty acids of the diacylglycerol and their influence on the HDL cholesterol level and PAI-1 activity. As a result, it has been found that a fat or oil composition has excellent HDL cholesterol elevating action and PAI-1 lowering action and is useful as an edible oil when there is a specific relationship among the kinds and amounts of the stereoisomers of the unsaturated fatty acid and the amount of the saturated fatty acid contained in the composition.

There is thus provided a fat or oil composition which comprises at least 35 wt. % of a diacylglycerol, the constituent fatty acids of said diacylglycerol satisfying the following equation: (an amount of a cis-form unsaturated fatty acid)/(an amount of a saturated fatty acid+an amount of a trans-form unsaturated fatty acid)$\geq 6$.

In another aspect of the present invention, there is also provided a fat or oil processed food comprising the above-described fat or oil composition.

In a further aspect of the present invention, there are also provided an HDL-cholesterol-level elevating agent and PAI-1-activity lowering agent, each comprising the above-described fat or oil composition.

In a still further aspect of the present invention, there are also provided a method for elevating the HDL cholesterol level in blood and a method for lowering the activity of PAI-1, each of which comprises administering the above-described fat or oil composition.

Intake of the fat or oil composition of the present invention usually as an edible oil makes it possible to reduce the blood level of an arteriosclerotic factor, leading to the prevention of arteriosclerosis and furthermore, various geriatric diseases.

DETAILED DESCRIPTION OF THE PREFERRED EMBODIMENTS

The fat or oil composition according to the present invention contains at least 35 wt. % (which will hereinafter be indicated simply as "%") of a diacylglycerol. From the viewpoints of effects for suppressing an increase in the blood level of a neutral fat, HDL cholesterol elevating action and PAI-1 lowering action, the diacylglycerol content is preferably at least 50%, with at least 60% being more preferred and with at least 80% being particularly preferred.

The constituent fatty acids of the diacylglycerol contained in the fat or oil composition of the present invention satisfy the following equation: (an amount of a cis-form unsaturated fatty acid)/(an amount of a saturated fatty acid+an amount of a trans-form unsaturated fatty acid)$\geq 6$. When this weight ratio of [(cis)/(trans+saturated)] is less than 6, the HDL cholesterol elevating effects and PAI-1 lowering effects both lower. The weight ratio of [(cis)/(trans+saturated)] is preferably at least 8 and more preferably at least 9. The amount of the trans-form unsaturated fatty acid not greater than 5% is particularly preferred and also the amount of the saturated fatty acid not greater than 5% is particularly preferred, each based on the amount of the constituent fatty acids of the diacylglycerol. Examples of the cis-form unsaturated fatty acid include oleic acid, α-linoleic acid, α-linolenic acid, cis-dihomo-γ-linolenic acid, cis-arachidonic acid, cis-eicosapentaenoic acid and cis-docosahexanoic acid. The term "trans-form unsaturated fatty acid" as used herein means an unsaturated fatty acid having, in the molecule thereof, at least one trans-form double bond. Examples of the saturated fatty acids include palmitic acid, stearic acid and arachic acid. Fatty acids having 8 to 24 carbon atoms are preferred, with those having 16 to 22 carbon atoms being particularly preferred. As the diacylglycerol, either one of 1,2-diacylglycerol or 1,3-diacylglycerol can be employed, with the 1,3-diacylglycerol being particularly preferred.

A phytosterol is a component having effects for lowering the cholesterol level and is contained in the conventional plant oil in an amount of about 0.05 to 1.2%. With a view to obtaining the cholesterol lowering effects equivalent to those of such a plant oil, the content of phytosterol is preferably at least 0.05%, with at least 0.3% being particularly preferred. The phytosterol content in the fat or oil composition containing a diacylglycerol differs depending on the preparation process of the composition. When a commercially available fatty acid obtained by distillation is used as a raw material, the phytosterol content in the composition inevitably lowers. In such a case, it is preferred to add a phytosterol to give an amount of 0.05% or greater. No particular limitation is imposed on the upper limit of the phytosterol content. For the purpose of attaining cholesterol reduction equal to that brought by the use of the conventional plant oil, the phytosterol content falling within a range of 0.05 to 1.2% is sufficient. When the more cholesterol level reduction is intended, at least 1.2% of phytosterol can be added. Examples of the phytosterol include phytosterols in the free form such as α-sitosterol, β-sitosterol, stigmasterol, campesterol, α-sitostanol, β-sitostanol, stigmastanol, campestanol and cycloartenol and esters thereof such as fatty acid esters, ferulic acid esters, and cinnamic acid esters.

The other components contained in the fat or oil composition of the present invention are a triacyl glycerol and a monoacyl glycerol. The monoacyl glycerol content not greater than 2%, particularly not greater than 1.5% is preferred. Most of the remaining part is composed of a triacyl glycerol.

The fat or oil composition according to the present invention can be prepared, for example, by subjecting fat or oil containing desired constituent fatty acids and glycerin to transesterification; or by acting lipase on a mixture of desired constituent fatty acids or ester thereof with glycerin, thereby carrying out esterification. The esterification using lipase is preferred for preventing isomerization during the reaction. Even in the esterification by using lipase, with a view to preventing isomerization upon purification after completion of the reaction, it is preferred to carry the purification under conditions mild enough not to cause isomerization of the fatty acids.

It is possible to incorporate, in the fat or oil composition of the present invention, a component contained in the conventional fat or oil composition, for example, an antioxidant such as tocopherol, ascorbyl palmitate, ascorbyl stearate, BHT, BHA or phospholipid and/or emulsifier such as sucrose fatty acid ester, polyglycerin fatty acid ester or organic acid monoglyceride.

As described above, the fat or oil composition according to the present invention has HDL cholesterol elevating action and PAI-1 lowering action. Although the use of a diacylglycerol ordinarily causes an increase in the melting point compared with the use of a triacyl glycerol composed of the same fatty acids, the fat or oil composition according to the present invention is able to have a liquid form at room temperature, which brings about an advantage that it is usable widely as an edible oil. The fat or oil composition according to the present invention can therefore be used suitably as a cooking oil. It can also be used as an oil-in-water type processed food such as beverage, dessert, ice cream, dressing, topping, mayonnaise or barbecue sauce; a water-in-oil type processed food such as margarine or spread; or a processed food such as peanut butter, frying oil or shortening. In addition, it can be used for processed foods such as potato chips, snacks, cakes, cookies, pies, bread or chocolates; bakery mix; processed meat products; frozen entree; frozen foods; or the like.

A description will next be made of the application of the fat or oil composition of the present invention to a fat or oil processed food.

In the fat or oil processed food of the present invention, the amount of the fat or oil (total amount of edible oil and diacylglycerol) in the food is 3 to 95% and the amount of phytosterol is at least 0.05% based on the total amount of the fat or oil. The diacylglycerol content in the fat or oil is at least 35%, more preferably at least 50%.

The term "fat or oil processed food" as used herein means a processed food obtained by adding, to the above-described fat or oil composition, the other food raw materials. The following raw materials are usable as components for the fat or oil processed food.

(1) Edible Fats or Oils
There is no particular limitation imposed on the edible fat or oil used in the present invention insofar as it is a commonly used edible fat or oil. Examples include natural animal or vegetable fats or oils; and processed fats or oils obtained by subjecting them to transesterification, hydrogenation, fractionation or the like. Preferred examples include vegetable oils such as soybean oil, rapeseed oil, rice bran oil, corn oil, sunflower oil, palm oil, palm kernel oil and coconut oil; and processed fats or oils thereof.

(2) Emulsifiers
There is no particular limitation imposed on the emulsifier insofar as it is commonly used for food. Examples include sucrose fatty acid esters, sorbitan fatty acid esters, glycerin fatty acid esters, lecithin and decomposed product thereof; and proteins such as egg protein, soybean protein and milk protein and various proteins available therefrom by separation or hydrolysis.

(3) Thickeners
There is no particular limitation imposed on the thickener insofar as it is commonly used for food. Examples include xanthan gum, gellan gum, guar gum, carrageenan, pectin, tragacanth gum, polysaccharides such as various starches and proteins such as gelatin and albumen.

(4) Various Seasonings Such as Salt, Sugar and Vinegar.
(5) Various Spices and Flavors.
(6) Various Coloring Matters.
(6) Antioxidants such as Tocopherol and Natural Antioxidant Components.

The preferred formulation examples of the present invention will hereinafter be described. It should however be borne in mind that the application of the fat or oil composition of the present invention is not limited by them.

1) Acidic oil-in-water type fat or oil processed food
  oil phase/water phase 20/80 to 80/20
  amount of diacylglycerol: at least 35% (preferably at least 50%) based on the amount of the fat or oil in the oil phase
  amount of phytosterol: at least 0.05% based on the amount of the fat or oil in the oil phase
  amount of emulsifier: 0.05 to 5%
  pH: 2 to 6.

The pH is adjusted by an organic acid such as citric acid or salt thereof, or an acidifier such as lemon juice. From the above-described materials, an acidic oil-in-water type fat or oil processed food such as dressing or mayonnaise which has HDL elevating effects and PAI-1 lowering effects and is free from problems in appearance, taste, texture and the like can be prepared in a conventional manner.

(Formulation Example) Mayonnaise

|  | parts by weight |
|---|---|
| Water phase | |
| Salt | 3.0 |
| Soft sugar | 1.0 |
| Seasoning (sodium glutamate) | 0.5 |
| Spice (mustard powder) | 0.3 |
| Yolk | 14 |
| Vinegar (10% acidity) | 8 |
| Thickener | 0.5 |
| Water | 22.7 |
| Oil phase | |
| fat or oil composition A | 50 |

2) Water-in-oil type spreadable fat or oil processed food
  oil phase/water phase : 90/10 to 10/90 (preferably 85/15 to 50/50)
  amount of diacylglycerol: at least 35% (preferably at least 50%) based on the amount of the fat or oil in the oil phase
  amount of phytosterol: at least 0.05% based on the amount of the fat or oil in the oil phase
  melting point of the fat or oil in the oil phase: 20 to 50° C. (preferably 20 to 40° C.).

From the above-described materials, a water-in-oil type spreadable fat or oil processed food which has HDL elevating effects and PAI-1 lowering effects and is free from problems in texture, spreadability and the like can be prepared in a conventional manner.

(Formulation Example) Spread

|  | (parts by weight) |
|---|---|
| Oil phase | |
| Fat or oil | 69.3 |
| Lecithin | 0.1 |
| Monoacyl glycerol | 0.5 |
| Flavor | 0.1 |
| Water phase | |
| Water | 28.4 |
| Skim milk | 0.3 |
| Salt | 1.3 |

*Fat or oil: fat or oil composition A: 70% / partially hydrogenated palm oil (IV = 40): 30%, melting point: 34.8° C.

3) Baked Cakes amount of fat or oil: 10 to 40% amount of diacylglycerol: at least 35% (preferably at least 50%) relative to the amount of the fat or oil amount of phytosterol: at least 0.05% relative to the amount of the fat or oil flour: 20 to 65% sugar: 5 to 30% whole egg: 0 to 20% salt: 0.1 to 2% baking powder: 0 to 1%

From the above-described materials, various baked cakes such as short bread which have HDL elevating effects and PAI-1 lowering effects can be prepared in a conventional manner.

(Formulation Example) Short Bread

|  | (parts by weight) |
|---|---|
| Flour | 60 |
| Fat or oil composition A | 10 |
| Sugar | 24.6 |
| Salt | 0.4 |
| Whole egg | 5 |

EXAMPLE 1

The fatty acid obtained by hydrolysis of a commercially available soybean oil having a trans fatty acid content of 0.8% was winterized to reduce the content of the saturated fatty acid. The resulting fatty acid was reacted with glycerin at 40° C. in the presence of a commercially available immobilized 1,3-specific lipase ("Lipozyme 3A"; product of Novo Nordisk A/S) as a catalyst. After the lipase preparation was filtered off, the residue was subjected to molecular distillation, followed by purification in a conventional manner, whereby a fat or oil composition A was obtained.

EXAMPLE 2

The fatty acid obtained by hydrolysis of a commercially available rapeseed oil having a trans fatty acid content of 0.6% was reacted with glycerin at 40° C. in the presence of a commercially available immobilized 1,3-specific lipase as a catalyst. After the lipase preparation was filtered off, the residue was subjected to molecular distillation, followed by purification in a conventional manner, whereby a fat or oil composition B was obtained.

EXAMPLE 3

A fat or oil composition C was obtained by mixing the fat or oil composition A and fat or oil composition B at a ratio of 7:3.

EXAMPLE 4

A fat or oil composition D was obtained by mixing the fat or oil composition A and a commercially available soybean oil at a ratio of 6:4.

COMPARATIVE EXAMPLE 1

The fatty acid obtained by hydrolysis of a commercially available soybean oil having a trans fatty acid content of 2.5% was reacted with glycerin at 40° C. in the presence of a commercially available immobilized 1,3-specific lipase as a catalyst. After the lipase preparation was filtered off, the residue was subjected to molecular distillation, followed by purification in a conventional manner, whereby a fat or oil composition E was obtained.

COMPARATIVE EXAMPLE 2

The fatty acid obtained by hydrolysis of a commercially available rapeseed oil having a trans fatty acid content of 2.8% was reacted with glycerin at 40° C. in the presence of a commercially available immobilized 1,3-specific lipase as a catalyst. After the lipase preparation was filtered off, the residue was subjected to molecular distillation, followed by purification in a conventional manner, whereby a fat or oil composition F was obtained.

The glyceride composition and constituent fatty acids of the diacylglycerol of each of the fat or oil compositions obtained in Examples 1 to 4 and Comparative Examples 1 and 2, and a soybean oil (Comparative Example 3) are shown in Tables 1 and 2.

[Measurement of Glyceride Distribution]

Each of the fat or oil compositions was silylated by a silylating agent ("silylating agent TH", product of Kanto Chemical), followed by analysis through gas chromatography by using a capillary column ("DBTM-1", trade name; product of J&W Scientific Incorporated).

[Distribution of Constituent Fatty Acids of Diacylglycerol]

Diacylglycerol fractions in each of the fat or oil compositions were collected by column chromatogram [after the removal of the triglyceride fractions by using "Wakogel C-200"(product of Wako Pure Chemicals Co., Ltd.) and hexane, diacylglycerol fractions were obtained using a 70:30 mixed solvent of hexane and ether]. After methylesterification in a conventional manner, analysis was carried out by gas chromatography with a capillary column ("CP-SIL88", trade name; product of Chrompack International BV).

TABLE 1

| Fat or oil composition | Glyceride Composition (%) | | | Phytosterol |
|---|---|---|---|---|
| | MG | DG | TG | |
| A | 1.0 | 85.5 | 13.1 | 0.4 |
| B | 1.2 | 84.7 | 13.1 | 1.0 |
| C | 0.9 | 85.1 | 13.4 | 0.6 |
| D | 0.6 | 51.8 | 47.2 | 0.4 |
| E | 0.9 | 83.1 | 15.7 | 0.3 |
| F | 1.3 | 81.9 | 15.9 | 0.9 |
| Soybean oil | ND | 1.0 | 98.7 | 0.3 |

TABLE 2

Composition of fatty acids (%)

| Constituent fatty acids of diacylglycerol | | Composition | | | | | | Commercially-available soybean oil |
|---|---|---|---|---|---|---|---|---|
| | | A | B | C | D | E | F | |
| C16 | | 2.5 | 4.1 | 3.0 | 5.8 | 10.8 | 4.2 | 10.8 |
| C18 | | 0.8 | 2.1 | 1.2 | 2.2 | 4.2 | 2.1 | 4.2 |
| C18:1 | cis | 27.8 | 60.9 | 37.7 | 26.4 | 24.4 | 56.8 | 24.4 |
| | trans | 0.0 | 0.0 | 0.0 | 0.0 | 0.0 | 1.2 | 0.0 |
| C18:2 | cis | 59.8 | 19.8 | 47.8 | 56.4 | 49.5 | 19.9 | 51.3 |
| | trans | 0.6 | 0.3 | 0.5 | 0.5 | 2.2 | 2.6 | 0.3 |
| C18:3 | cis | 6.7 | 8.4 | 7.2 | 6.7 | 4.0 | 6.0 | 6.7 |
| | trans | 1.0 | 1.4 | 1.1 | 0.8 | 3.2 | 4.1 | 0.5 |
| C20 | | 0.0 | 0.7 | 0.2 | 0.2 | 0.4 | 0.9 | 0.4 |
| uk | | 0.8 | 2.3 | 1.2 | 1.0 | 1.3 | 2.2 | 1.4 |
| trans | | 1.6 | 1.7 | 1.6 | 1.3 | 5.4 | 7.9 | 0.8 |
| saturated | | 3.3 | 6.9 | 4.4 | 8.2 | 15.4 | 7.2 | 15.4 |
| trans + saturated | | 4.9 | 8.6 | 6.0 | 9.5 | 20.8 | 15.1 | 16.2 |
| cis | | 94.3 | 89.1 | 92.7 | 89.5 | 77.9 | 82.7 | 82.4 |
| cis/(trans + saturated) | | 19.1 | 10.4 | 15.5 | 9.4 | 3.7 | 5.5 | 5.1 | uk: unknown component

Test 1

Instead of the edible oil usually employed, each of the fat or oil compositions was used for three months. Daily intake of it was 12.5 g. Male and female adults, 10 in total, whose total cholesterol level tended to be high were tested. Effects, on the total cholesterol level and HDL cholesterol level, of each of the fat or oil compositions obtained in Examples and Comparative Examples are shown in Table 3. The effects are indicated by a value relative to the initial value set at 100. In each group, no change was observed from the total cholesterol level before the test to that after the test.

TABLE 3

| | Fat or oil composition | cis/(saturated + trans) | Total cholesterol level | HDL cholesterol level |
|---|---|---|---|---|
| Example 1 | A | 19.1 | 99.3 | 111.9 |
| Example 2 | B | 10.4 | 100.1 | 109.8 |
| Example 3 | C | 15.5 | 99.8 | 110.5 |
| Example 4 | D | 9.4 | 100.3 | 108.2 |
| Comp. Ex. 1 | E | 3.7 | 101.1 | 102.5 |
| Comp. Ex. 2 | F | 5.5 | 98.9 | 103.0 |
| Comp. Ex. 3 | soybean oil | 5.1 | 102.0 | 98.2 |

Test 2

Instead of the edible oil usually employed, each of the fat or oil compositions was used for three months. Daily intake of it was 12.5 g. Male and female adults, 8 in total, whose total cholesterol level tended to be high were tested. Effects, on PAI-1, of each of the fat or oil compositions obtained in Examples and Comparative Examples are shown in Table 4. The effects are indicated by a value relative to the initial value set at 100.

TABLE 4

| | Fat or oil composition | cis/(saturated + trans) | PAI-1 |
|---|---|---|---|
| Example 1 | A | 19.1 | 82.0 |
| Example 2 | B | 10.4 | 85.7 |
| Example 3 | C | 15.5 | 84.1 |
| Example 4 | D | 9.4 | 87.9 |
| Comp. Ex. 1 | E | 3.7 | 94.0 |
| Comp. Ex. 2 | F | 5.5 | 93.1 |
| Comp. Ex. 3 | soybean oil | 5.1 | 105.5 |

What is claimed is:

1. A fat or oil composition which comprises at least 35 wt. % of a diacylglycerol, the constituent fatty acids of said diacylglycerol satisfying the following equation: (an amount of a cis-form unsaturated fatty acid)/(an amount of a saturated fatty acid+an amount of a trans-form unsaturated fatty acid)≧6, wherein the amount of the trans-form unsaturated acid is not greater than 5 wt % based on the constituent fatty acids of said diacylglycerol, and further comprising phytosterol in an amount of not less than 0.05 wt %, wherein administration of an effective amount of the composition to a subject increases the HDL cholesterol level in said subject.

2. A fat or oil composition according to claim 1, wherein the constituent fatty acids of said diacylglycerol satisfy the following equation: (an amount of a cis-form unsaturated fatty acid)/(an amount of a saturated fatty acid+an amount of a trans-form unsaturated fatty acid)≧9.

3. A fat or oil composition according to claim 1, wherein the amount of the saturated fatty acid is not greater than 5 wt. % based on the constituent fatty acids of said diacylglycerol.

4. A fat or oil processed food comprising a fat or oil composition as claimed in claim 1.

5. A PAI-1-activity lowering agent comprising a fat or oil composition as claimed in claim 1.

6. A method foe evaluating the HDL cholesterol level in the blood of a patient in need thereof, comprising administering to said patient in need thereof, a fat or oil composition as claimed in claim 1.

7. A method for lowering the activity of PAI-1 in a patient in need thereof, comprising administering to said patient in need thereof, a fat or oil composition as claimed in claim 1.

8. A fat or oil composition which comprises at least 80 wt % of a diacylglycerol, the constituent fatty acids of said diacylglycerol satisfying the following equation: (an amount of a cis-form unsaturated fatty acid)/(an amount of a saturated fatty acid+an amount of a trans-form unsaturated fatty acid) ≧ 6, wherein the amount of the trans-form unsaturated acid is not greater than 5 wt % based on the constituent fatty acids of said diacylglycerol, wherein administration of an effective amount of the composition to a subject increases the HDL cholesterol level in said subject.

9. A fat or oil composition according to claim 8, which further comprises phytosterol in an amount not less than 0.05 wt %.

10. A fat or oil composition according to claim 8, wherein the constituent fatty acids of said diacylglycerol satisfy the following equation: (an amount of a cis-form unsaturated fatty acid)/(an amount of a saturated fatty acid+an amount of a trans-form unsaturated fatty acid)≧9.

11. A fat or oil composition according to claim 8, wherein the amount of the saturated fatty acid is not greater than 5 wt % based on the constituent fatty acids of said diacylglycerol.

12. A fat or oil processed food comprising a fat or oil composition as claimed in claim 8.

13. A PAI-1-activity lowering agent comprising a fat or oil composition as claimed in claim 8.

14. A method for evaluating the HDL cholesterol level in the blood of a patient in need thereof, comprising administering to said patient in need thereof, a fat or oil composition as claimed in claim 8.

15. A method for lowering the activity of PAI-1 in a patient in need thereof, comprising administering to said patient in need thereof, a fat or oil composition as claimed in claim 8.

16. A fat or oil processed food, comprising:

(a) one or more food raw materials;

(b) a fat or oil comprising at least 35 wt % of a diacylglycerol, the constituent fatty acids of said diacylglycerol satisfying the following equation: (an amount of a cis-form unsaturated fatty acid)/(an amount of a saturated fatty acid+an amount of a trans-form unsaturated fatty acid)≧6, wherein the amount of the trans-form unsaturated acid is not greater than 5 wt % based on the constituent fatty acids of said diacylglycerol; and (c) phytosterol in an amount of not less than 0.05 wt %, based on total amount of said fat or oil (b), wherein consumption of an effective amount of the food by a subject increases the HDL cholesterol level in said subject.

* * * * *